US012016537B2

(12) United States Patent
Wang et al.

(10) Patent No.: US 12,016,537 B2
(45) Date of Patent: Jun. 25, 2024

(54) SPONGE-BASED VARIABLE-STIFFNESS SUPPORT STRUCTURE FOR NATURAL ORIFICE SURGICAL INSTRUMENT AND METHOD FOR USING THE SAME

(71) Applicant: TIANJIN UNIVERSITY, Tianjin (CN)

(72) Inventors: Shuxin Wang, Tianjin (CN); Xuyang Ren, Tianjin (CN); Guokai Zhang, Tianjin (CN); Zufeng Shang, Tianjin (CN); Jinhua Li, Tianjin (CN)

(73) Assignee: Tianjin University, Tianjin (CN)

( * ) Notice: Subject to any disclaimer, the term of this patent is extended or adjusted under 35 U.S.C. 154(b) by 967 days.

(21) Appl. No.: 15/733,576

(22) PCT Filed: Jun. 29, 2018

(86) PCT No.: PCT/CN2018/093599
§ 371 (c)(1),
(2) Date: Sep. 2, 2020

(87) PCT Pub. No.: WO2019/205277
PCT Pub. Date: Oct. 31, 2019

(65) Prior Publication Data
US 2021/0000460 A1  Jan. 7, 2021

(30) Foreign Application Priority Data

Apr. 24, 2018 (CN) .......................... 201810371746.1

(51) Int. Cl.
*A61B 17/00* (2006.01)
*A61B 17/12* (2006.01)
(Continued)

(52) U.S. Cl.
CPC .. *A61B 17/00234* (2013.01); *A61B 2017/003* (2013.01); *A61B 2017/00305* (2013.01);
(Continued)

(58) Field of Classification Search
CPC .... A61B 2017/003; A61B 2017/00305; A61B 2017/00539; A61B 2017/00544;
(Continued)

(56) References Cited

U.S. PATENT DOCUMENTS 5,100,384 A * 3/1992 McBrien ............... A61M 25/10
604/99.01
9,844,378 B2 12/2017 Casasanta et al.
(Continued)

FOREIGN PATENT DOCUMENTS

CN    101170965 A    4/2008
CN    104825229 A    8/2015
(Continued)

OTHER PUBLICATIONS

"International Application Serial No. PCT/CN2018/093599, International Search Report mailed Jan. 22, 2019", (Jan. 22, 2019), 4 pgs.
(Continued)

*Primary Examiner* — Marcela I. Shirsat
(74) *Attorney, Agent, or Firm* — Schwegman Lundberg & Woessner, P.A.

(57) ABSTRACT

A sponge-based variable-stiffness support structure for natural orifice surgical instrument is to support the surgical instrument and includes: a variable-stiffness sponge pipeline connected with the natural orifice surgical instrument and configured to support the natural orifice surgical instrument in a natural orifice; a hydrophobic breathable film attached to an outer wall of the variable-stiffness sponge pipeline, and configured to isolate the variable-stiffness sponge pipeline from body fluid in the natural orifice; and a gas delivery assembly connected with the variable-stiffness sponge pipeline, and configured to inject high-pressure air or water vapor into a variable-stiffness sponge pipe of the variable-stiffness sponge pipeline; wherein the variable-stiffness
(Continued)

sponge pipeline has a stiffness inversely proportional to content of the water vapor.

13 Claims, 3 Drawing Sheets

(51) Int. Cl.
*A61B 17/32* (2006.01)
*A61B 17/34* (2006.01)

(52) U.S. Cl.
CPC .............. *A61B 2017/00938* (2013.01); *A61B 17/12013* (2013.01); *A61B 17/320016* (2013.01); *A61B 17/3415* (2013.01); *A61B 2017/3419* (2013.01); *A61B 17/3421* (2013.01); *A61B 2017/3429* (2013.01); *A61B 2017/3445* (2013.01); *A61B 2017/345* (2013.01); *A61B 2017/3452* (2013.01); *A61B 17/3494* (2013.01); *A61B 17/3496* (2013.01)

(58) Field of Classification Search
CPC .......... A61B 2017/00566; A61B 2017/00898; A61B 2017/00938; A61B 2017/00942; A61B 2017/00943; A61B 2017/3419; A61B 2017/3429; A61B 2017/3445; A61B 2017/345; A61B 2017/3452; A61B 34/72; A61B 1/00064; A61B 1/00071; A61B 1/005; A61B 1/0052; A61B 1/0055; A61B 1/012; A61B 1/0125; A61B 2090/701
USPC ................. 600/207, 201, 203–206, 229, 235
See application file for complete search history.

(56) References Cited

U.S. PATENT DOCUMENTS

| 10,058,413 | B2 | 8/2018 | Heiss |
| 2005/0119613 | A1* | 6/2005 | Moenning ............ A61M 31/00 604/93.01 |
| 2007/0043428 | A1 | 2/2007 | Jennings et al. |
| 2009/0062614 | A1 | 3/2009 | Adzich et al. |
| 2010/0179644 | A1 | 7/2010 | Jennings et al. |
| 2013/0190706 | A1* | 7/2013 | Kleiner ................. A61M 1/916 604/319 |
| 2015/0250979 | A1* | 9/2015 | Loske ............... A61M 25/0074 604/315 |
| 2015/0305743 | A1 | 10/2015 | Casasanta et al. |
| 2016/0296295 | A1 | 10/2016 | Piligian et al. |
| 2016/0367352 | A1* | 12/2016 | Heiss ....................... A61F 2/04 |
| 2019/0008630 | A1 | 1/2019 | Heiss |

FOREIGN PATENT DOCUMENTS

| CN | 105011978 A | 11/2015 |
| CN | 105796137 A | 7/2016 |
| CN | 105916467 A | 8/2016 |
| CN | 106037935 A | 10/2016 |
| CN | 205924670 U | 2/2017 |
| CN | 107280716 A | 10/2017 |
| CN | 107280718 A | 10/2017 |
| CN | 107349014 A | 11/2017 |
| WO | WO-2013026012 A1 | 2/2013 |

OTHER PUBLICATIONS

"International Application Serial No. PCT/CN2018/093599, Written Opinion mailed Jan. 22, 2019", w/ English Translation, (Jan. 22, 2019), 7 pgs.

"Chinese Application Serial No. 201810371746.1, Office Action mailed Jun. 3, 2019", w/ English Translation, (Jun. 3, 2019), 10 pgs.

"Chinese Application Serial No. 201810371746.1, Office Action mailed Nov. 4, 2019", w/ English Translation, (Nov. 4, 2019), 11 pgs.

* cited by examiner

SPONGE-BASED VARIABLE-STIFFNESS SUPPORT STRUCTURE FOR NATURAL ORIFICE SURGICAL INSTRUMENT AND METHOD FOR USING THE SAME

PRIORITY APPLICATIONS

This application is a U.S. National Stage Filing under 35 U.S.C. § 371 from International Application No. PCT/CN2018/093599, filed on Jun. 29, 2018, and published as WO2019/205277 on Oct. 31, 2019, which claims the benefit of priority to Chinese Application No. 201810371746.1, filed on Apr. 24, 2018; the benefit of priority of each of which is hereby claimed herein, and which applications and publication are hereby incorporated herein by reference in their entireties.

FIELD OF THE INVENTION

The present disclosure relates to a field of natural orifice surgical instrument, and more particularly to a sponge-based variable-stiffness support structure for natural orifice surgical instrument and a method for using the same.

BACKGROUND

A natural orifice transluminal endoscopic surgery (NOTES) is a new research hotspot in a surgical field after multiport minimally invasive surgery and single port minimally invasive surgery. In such a surgery, a surgical instrument is inserted into an abdomen via a natural orifice of human body, such as mouth, colorectum, and bladder, etc., to treat a disease. It is a scar-free operation without any incision on body surface. The natural orifice transluminal minimally invasive surgery does not leave any incision in a human body surface during treating a patient's disease, thereby mitigating a surgical trauma and postoperative pain and increasing a cosmetic effect, thus achieving better physiological and psychological minimally invasive effects.

Most of the surgical instruments currently used are master-slave type operation instruments. Only micro-surgical tools are delivered to a targeted site. A doctor operates remotely by a control mechanism, and the control mechanism is connected to an actuator through a pipeline. In order to adapt for a tortuous body orifice, the pipeline connected between the control mechanism and the actuator is required to be formed into a flexible rod. The surgical tool is fixed at a remote end of the pipeline and is delivered to the targeted site through the body orifice. The pipeline assists the surgical tool for cutting, suturing, knotting, rinsing and other surgical operations. Then, after the operation is completed, the surgical tool is retracted along the natural orifice.

However, during implementing the present disclosure, inventors of the present disclosure have found that during access to the targeted site through the natural body orifice, flexibility of the current pipeline for surgical instrument is insufficient, which will cause damage to the natural orifice; and due to insufficient flexibility, it is rather difficult to achieve certain postures in a process of adjusting a posture of the surgical tool before the operation. At the same time, a stable operating environment is required during the surgical operation, and thus it is required for the pipeline for surgical instrument to provide a stable and reliable support. However, stiffness of the current pipeline for surgical instrument is not enough to ensure stability and accuracy of the operation.

SUMMARY OF THE INVENTION

The present disclosure provides a sponge-based variable-stiffness support structure for natural orifice surgical instrument and a method for using the same, so as to alleviate technical problems in the relevant art that the pipeline of natural orifice surgical instrument for human body is not flexible enough, thus it is easy to cause damage to the natural orifice, and the stiffness is not enough to ensure the stability and accuracy of the operation.

An embodiment of the present disclosure provides a sponge-based variable-stiffness support structure for natural orifice surgical instrument, configured to support the natural orifice surgical instrument and including: a variable-stiffness sponge pipeline connected with the natural orifice surgical instrument and configured to support the surgical instrument in a natural orifice; a hydrophobic breathable film attached to an outer wall of the variable-stiffness sponge pipeline, and configured to isolate the variable-stiffness sponge pipeline from body fluid in the natural orifice; and a gas delivery assembly connected with the variable-stiffness sponge pipeline, and configured to inject high-pressure air or water vapor into a variable-stiffness sponge pipe of the variable-stiffness sponge pipeline; wherein the variable-stiffness sponge pipeline has a stiffness inversely proportional to content of the water vapor.

In some embodiments of the present disclosure, a spring skeleton is provided in the variable-stiffness sponge pipe of the variable-stiffness sponge pipeline and configured to support the variable-stiffness sponge pipeline.

In some embodiments of the present disclosure, the spring skeleton is made of stainless steel, and a surface of the spring skeleton is coated with an insulating coating.

In some embodiments of the present disclosure, an inner wall of the variable-stiffness sponge pipeline is provided with the hydrophobic breathable film.

In some embodiments of the present disclosure, the gas delivery assembly includes a gas delivery device and a gas delivery line, the gas delivery device being connected with the variable-stiffness sponge pipeline through the gas delivery line, and the gas delivery line being located in the variable-stiffness sponge pipe of the variable-stiffness sponge pipeline.

In some embodiments of the present disclosure, the gas delivery device includes a water vapor generator configured to generate the water vapor therein and a gas pump configured to generate the high-pressure air.

In some embodiments of the present disclosure, a non-breathable film is attached locally to the variable-stiffness sponge pipeline and configured to isolate the water vapor from variable-stiffness sponge of the variable-stiffness sponge pipeline, so that they cannot contact with each other.

In some embodiments of the present disclosure, the variable-stiffness sponge pipeline has a cross-section of a circular ring, an elliptical ring, or an N-shaped ring where N≥3 and is an integer.

In some embodiments of the present disclosure, the variable-stiffness sponge of the variable-stiffness sponge pipeline is made of polyvinyl formal.

A further embodiment of the present disclosure provides a surgical instrument assembly, including: a natural orifice surgical instrument and a sponge-based variable-stiffness support structure for natural orifice surgical instrument as described in any of the above embodiments, the sponge-based variable-stiffness support structure for natural orifice surgical instrument being connected with the natural orifice surgical instrument to support the natural orifice surgical instrument.

A further another embodiment of the present disclosure provides a method for using a sponge-based variable-stiffness support structure for natural orifice surgical instrument, including: assembling the sponge-based variable-stiffness support structure for natural orifice surgical instrument as described in any of the above embodiments with the natural orifice surgical instrument; injecting water vapor into the variable-stiffness sponge pipeline through the gas delivery line to make the variable-stiffness sponge pipeline flexible, and inserting the natural orifice surgical instrument into the natural orifice; adjusting a posture of the natural orifice surgical instrument, and injecting high-pressure air into the variable-stiffness sponge pipeline through the gas delivery line to make the variable-stiffness sponge pipeline stiff to perform operation; after completing the operation, injecting the water vapor into the variable-stiffness sponge pipeline through the gas delivery line to make the variable-stiffness sponge pipeline return to being flexible, and retracting the surgical instrument from human body through the natural orifice.

In some embodiments of the present disclosure, the method further includes: attaching a non-breathable film to a portion of the variable-stiffness sponge pipeline that needs to be continuously maintained in a stiff state.

In some embodiments of the present disclosure, when the variable-stiffness sponge pipeline has an axial tensile elastic modulus between 0.09 and 10 MPa the variable-stiffness sponge pipeline is in a flexible state; and, when the variable-stiffness sponge pipeline has an axial tensile elastic modulus between 10 and 31 MPa, the variable-stiffness sponge pipeline is in a stiff state.

According to the embodiments, the present disclosure at least has following beneficial effects:

The variable-stiffness sponge pipeline has good stiff-flexible conversion characteristics. When being assembled with the surgical instrument, the variable-stiffness sponge pipeline may be made to become the flexible state in order to facilitate assembly. And, when the variable-stiffness sponge pipeline along with the surgical instrument is inserted into the natural orifice, the variable-stiffness sponge pipeline may protect human tissue from being scratched by the natural orifice surgical instrument, and may not add extra resistance in the surgical posture adjustment, which reduces the difficulty of posture adjustment. When the surgical operation is performed, the variable-stiffness sponge pipeline may be made to become the stiff state, in order to provide a stable operating platform to ensure stable and accurate surgical operation.

BRIEF DESCRIPTION OF THE DRAWINGS

The drawings are used to further understand the present disclosure and form a part of the description. They are intended to interpretate the present disclosure along with the detailed embodiments below, whereas should not be construed as being limited to the present disclosure. In the drawings.

LIST OF REFERENCE NUMERALS

1—sponge-based variable-stiffness support structure for natural orifice surgical instrument;
   10—variable-stiffness sponge pipeline;
   11—variable-stiffness sponge pipe;
   20, 21—hydrophobic breathable film;
   30—gas delivery device;
      31—water vapor generator;
      32—gas pump;
   40, 41—gas delivery line;
   50—spring skeleton;
   60—non-breathable film;
   70—gas delivery assembly;
2—natural orifice surgical instrument;
3—surgical instrument assembly.

DETAILED DESCRIPTION OF PREFERRED EMBODIMENTS OF THE INVENTION

The sponge-based variable-stiffness support structure for natural orifice surgical instrument and a method for using the same, provided by the embodiments of the present disclosure, utilize variable-stiffness sponge as a base of the support structure and adjust the stiffness of the variable-stiffness sponge, so as to reduce a risk of scratching the natural orifice of human body and ensure the stability of surgical instrument during the operation.

In order to make the objectives, technical solutions, and advantages of the present disclosure clearer, the present disclosure is further described below in detail with reference to specific embodiments and the accompanying drawings.

Figure 1:
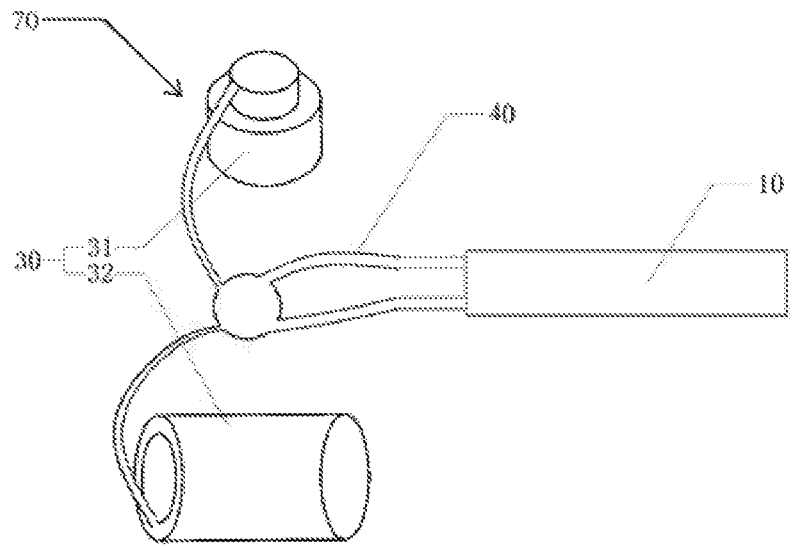
FIG. 1 is a schematic diagram of a sponge-based variable-stiffness support structure for natural orifice surgical instrument in the present disclosure.
Figure 2:
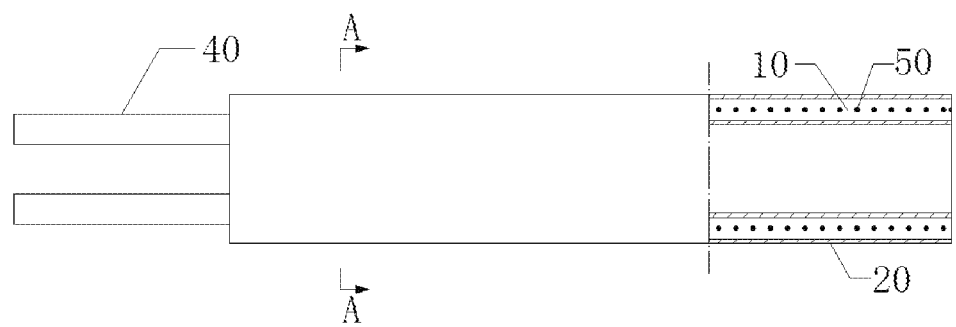
FIG. 2 is a schematic diagram illustrating connection of a variable-stiffness sponge pipeline and a gas delivery line in the support structure as shown in FIG. 1.
Figure 3:
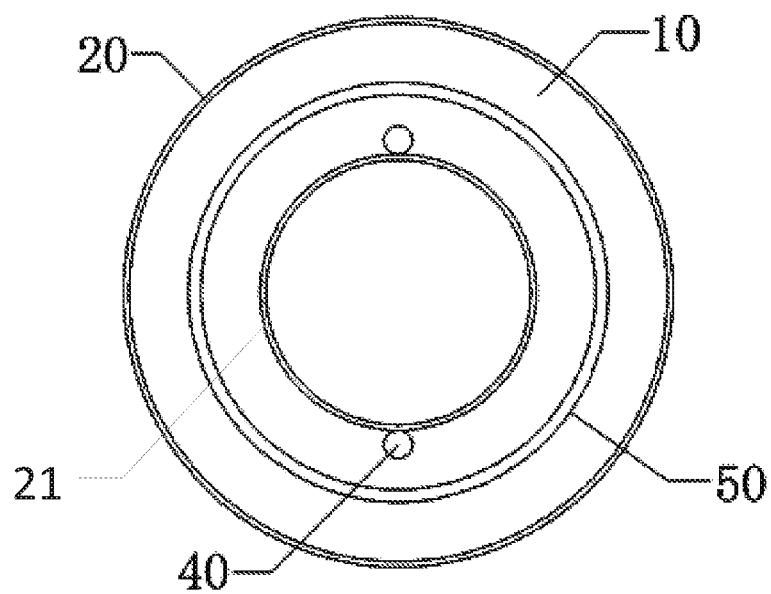
FIG. 3 is a cross-sectional view of the support structure as shown in FIG. 2 cut along a direction A-A thereof.

FIG. 1 is a schematic diagram of a sponge-based variable-stiffness support structure for natural orifice surgical instrument according to embodiments of the present disclosure. FIG. 2 is a schematic diagram illustrating connection of a variable-stiffness sponge pipeline and a gas delivery line in the support structure as shown in FIG. 1. FIG. 3 is a cross-sectional view of the support structure as shown in FIG. 2 cut along a direction A-A thereof.

An embodiment of the present disclosure provides a sponge-based variable-stiffness support structure 1 for natural orifice surgical instrument, as shown in FIGS. 1-3, including a variable-stiffness sponge pipeline 10 and a gas delivery assembly 70.

The variable-stiffness sponge pipeline 10 is made of variable stiffness sponge, connected with the surgical instrument 2 and configured to support it in the natural orifice. A hydrophobic breathable film 20 is attached to an outer wall of the variable-stiffness sponge pipeline 10 and configured to isolate the variable-stiffness sponge pipeline 10 from body fluid in the natural body orifice.

The gas delivery assembly 70 includes a gas delivery device 30 and a gas delivery line 40. The gas delivery device 30 is connected with the variable-stiffness sponge pipeline 10 by the gas delivery line 40. The gas delivery device 30 includes a water vapor generator 31 and a gas pump 32. The water vapor generator 31 may be configured to generate water vapor therein. The gas pump 32 may be configured to generate high-pressure air.

The gas delivery line 40 is inserted into a variable-stiffness sponge pipe 11 at an end of the variable-stiffness sponge pipeline 10. The water vapor generator 31 is used to inject water vapor into the variable-stiffness sponge pipe 11 of the variable-stiffness sponge pipeline 10 by the gas delivery line 40. The gas pump 32 is used to inject high-pressure air into the variable-stiffness sponge pipe 11 of the variable-stiffness sponge pipeline 10 by the gas delivery line 40.

The stiffness of the variable-stiffness sponge pipeline 10 is reduced with an increase of the content of the water vapor. Swelling principle of the variable-stiffness sponge is used to control the stiffness of the variable-stiffness sponge pipeline 10. When water vapor is introduced, the variable-stiffness sponge swells, intermolecular force decreases, the stiffness of the variable-stiffness sponge becomes smaller, and then the stiffness of the entire variable-stiffness sponge pipeline 10 becomes smaller; and when high-pressure air is introduced, the water vapor in the variable-stiffness sponge can be blown out so as to cause the sponge to reversely swell, molecular gap becomes smaller, and thus the stiffness of the entire variable-stiffness sponge pipeline 10 becomes larger.

The variable-stiffness sponge pipeline 10 has good stiff-flexible conversion characteristics. When being assembled with the surgical instrument 2, the variable-stiffness sponge pipeline may be made to become a flexible state in order to facilitate assembly. And, when the variable-stiffness sponge pipeline along with the surgical instrument 2 is inserted into the natural orifice, the variable-stiffness sponge pipeline may protect human tissue from being scratched by the natural orifice surgical instrument, and may not add extra resistance in the surgical posture adjustment, which reduces the difficulty of posture adjustment. When the surgical operation is performed, the variable-stiffness sponge pipeline 10 may be made to become a stiff state, in order to provide a stable operating platform to ensure stable and accurate surgical operation.

As shown in FIGS. 2-3, a spring skeleton 50 is provided in the variable-stiffness sponge pipeline 10 and configured to support the variable-stiffness sponge pipeline 10. The spring skeleton 50 is made of stainless-steel material. A surface of the spring skeleton 50 is coated with an insulating coating. The spring skeleton 50 enables the variable-stiffness sponge pipeline 10 not to be easily collapsed under a condition of large curvature deformation or radial compression, which would cause a hollow structure being blocked.

Further, an inner wall of the variable-stiffness sponge pipeline 10 is provided with a hydrophobic breathable film 21.

In some embodiments of the present disclosure, as shown in FIG. 3, the gas delivery line 40 is arranged in the variable-stiffness sponge pipe 11 of the variable-stiffness sponge pipeline 10 and close to the hydrophobic breathable film 21.

Figure 4:
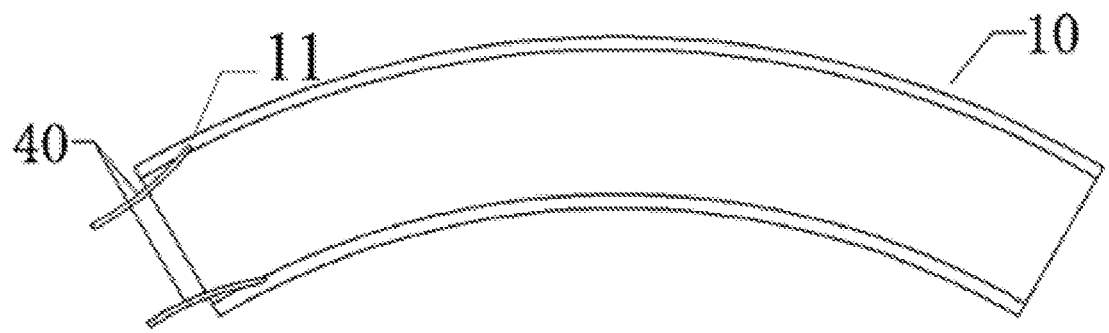
FIG. 4 is a schematic diagram illustrating overall bending of a variable-stiffness sponge pipeline in the support structure as shown in FIG. 1.
Figure 5:
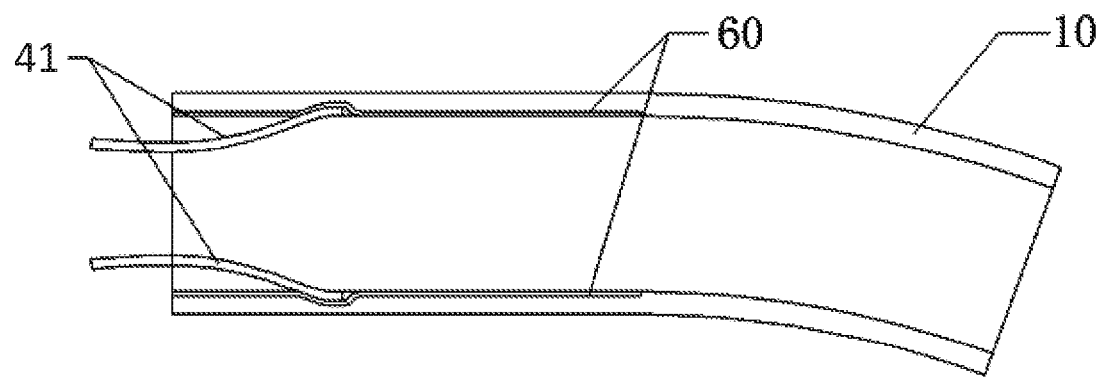
FIG. 5 is a schematic diagram illustrating local bending of a variable-stiffness sponge pipeline in the support structure as shown in FIG. 1.

FIG. 4 is a schematic diagram illustrating overall bending of a variable-stiffness sponge pipeline in the support structure as shown in FIG. 1. FIG. 5 is a schematic diagram illustrating local bending of a variable-stiffness sponge pipeline in the support structure as shown in FIG. 1.

As shown in FIGS. 4-5, a non-breathable film 60 is attached locally to the variable-stiffness sponge pipeline 10. The non-breathable film 60 may be attached locally to the inner wall of the variable-stiffness sponge pipeline 10. The non-breathable film 60 is set to isolate the water vapor from the variable-stiffness sponge of the variable-stiffness sponge pipeline 10, so that the variable-stiffness sponge pipeline 10 is locally bent.

In addition, the gas delivery assembly 70 of this embodiment may further include a group of gas delivery lines, including one or more gas delivery lines 41 which are respectively inserted into different positions of the variable-stiffness sponge pipe 11 of the variable-stiffness sponge pipeline 10. The local bending of the variable-stiffness sponge pipeline 10 is achieved by providing a local gas delivery line 41 on the variable-stiffness sponge pipeline 10 (changing an access point of the gas delivery line 41 to the variable-stiffness sponge pipeline 10). By providing the local gas delivery line 41 or attaching the non-breathable film 60 to the variable-stiffness sponge pipeline 10, an effect of local variable stiffness is achieved, and the stiffness of surgical instrument is segmentally and differentially controlled to meet the diversified requirements of surgery.

In this embodiment, the variable-stiffness sponge pipeline 10 has a cross-section of a circular ring, an elliptical ring, or an N-shaped ring where $N \leq 3$ and is an integer.

In this embodiment, the variable-stiffness sponge and the hydrophobic breathable film may be made of non-toxic materials with good tissue compatibility and suitable for the surgical instrument which is in contact with the body tissue. The variable-stiffness sponge preferably includes polyvinyl formal.

Figure 6:
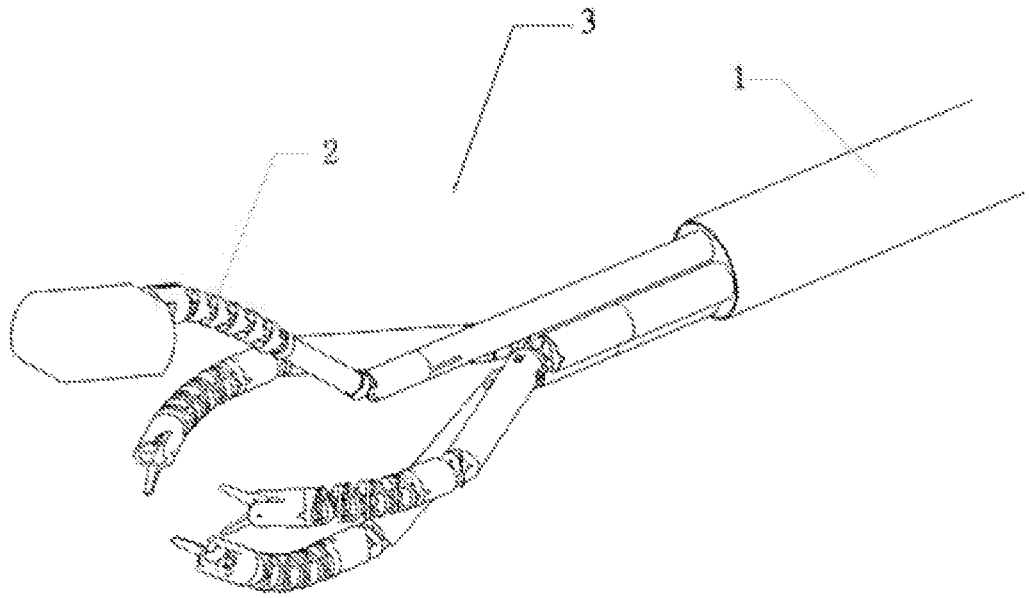
FIG. 6 is a schematic diagram illustrating connection of the support structure as shown in FIG. 1 with a natural orifice surgical instrument.

FIG. 6 is a schematic diagram illustrating connection of the support structure as shown in FIG. 1 with a natural orifice surgical instrument.

In another embodiment of the present disclosure, there is provided a surgical instrument assembly 3, as shown in FIG. 6, including: a natural orifice surgical instrument 2 and a sponge-based variable-stiffness support structure 1 for natural orifice surgical instrument. The variable-stiffness support structure for natural orifice surgical instrument adopts the support structure described above, and is connected with the natural orifice surgical instrument 2 to support the natural orifice surgical instrument 2.

Figure 7:
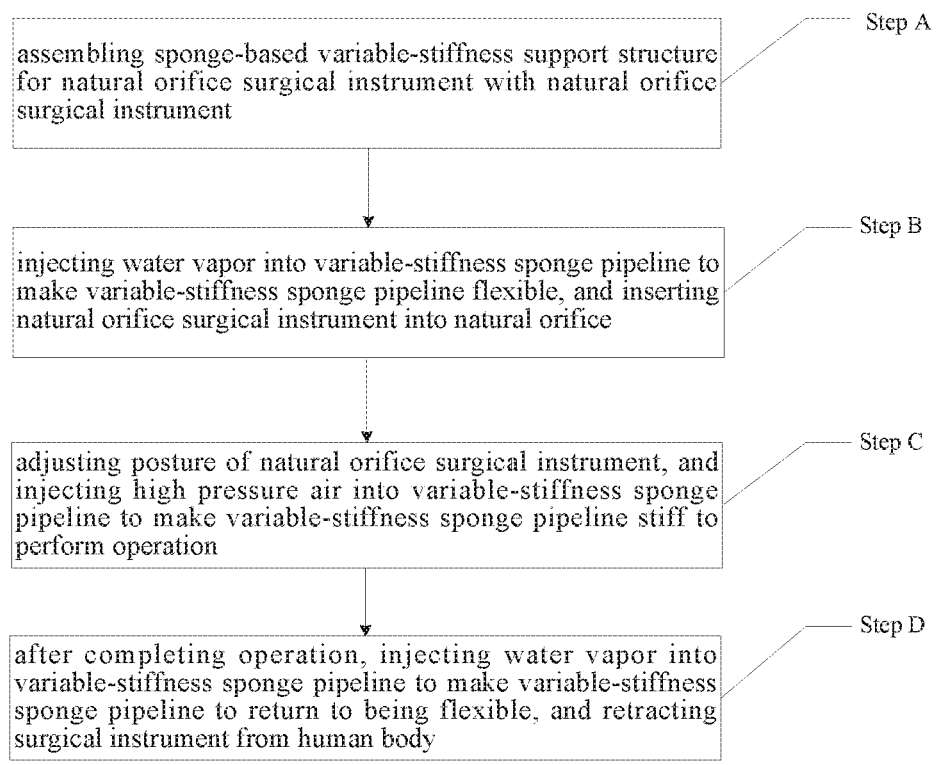
FIG. 7 is a flowchart of a method for using the sponge-based variable-stiffness support structure for natural orifice surgical instrument provided by the present disclosure.

FIG. 7 is a flowchart of a method for using the sponge-based variable-stiffness support structure for natural orifice surgical instrument provided by the present disclosure.

In another embodiment of the present disclosure, there is also provided a method for using a sponge-based variable-stiffness support structure for natural orifice surgical instrument, as shown in FIGS. 6-7, including: Step A: assembling the sponge-based variable-stiffness support structure 1 for natural orifice surgical instrument provided in any one of the embodiments of the present disclosure with the natural orifice surgical instrument 2; Step B: injecting water vapor into the variable-stiffness sponge pipeline 10 through the gas delivery line 40 to make the variable-stiffness sponge pipeline 10 flexible, and inserting the natural orifice surgical instrument 2 into the natural orifice; Step C: adjusting the posture of the natural orifice surgical instrument 2, and injecting high-pressure air into the variable-stiffness sponge pipeline 10 through the gas delivery line 40 to make the variable-stiffness sponge pipeline 10 stiff to perform operation; Step D: after completing the operation, injecting the water vapor into the variable-stiffness sponge pipeline 10 through the gas delivery line 40 to make the variable-stiffness sponge pipeline 10 return to being flexible again, and retracting the surgical instrument from human body through the natural orifice. This enables the variable-stiffness sponge pipeline 10 to be conversed between the flexible state and the stiff state by the water vapor and high-pressure air, which has fast response, has high conversion efficiency, and shortens the operation time effectively.

Further, the method for using a sponge-based variable-stiffness support structure for natural orifice surgical instrument further includes: Step E: attaching the non-breathable film 60 to a portion of the variable-stiffness sponge pipeline 10 that needs to be continuously maintained in the stiff state, so as to segmentally and differentially control the stiffness of the variable-stiffness sponge pipeline to satisfy the diversified requirements of surgery.

In this embodiment, when the variable-stiffness sponge pipeline 10 has an axial tensile elastic modulus between 0.09 and 10 MPa, the variable-stiffness sponge pipeline 10 is in the flexible state; and, when the variable-stiffness sponge pipeline 10 has an axial tensile elastic modulus between 10 and 31 MPa the variable-stiffness sponge pipeline 10 is in the stiff state.

It will be appreciated clearly by a person skilled in the art that for sake of brevity and clarity of description, each functional module is divided as described above, only taking as an example. In practical applications, the above-mentioned functions may be assigned to different functional modules as required, that is, internal structure of the device is divided into different functional modules to complete all or part of the functions described above. For the specific operation process of the device described above, reference may be made to the corresponding process in the foregoing method embodiments, and details are not described herein again.

Finally, it should be noted that the above embodiments are only intended to illustrate the technical solutions of the present disclosure, but not to limit them. Although reference is made to the above-mentioned embodiments to describe the present disclosure in detail, it would be appreciated by those skilled in the art that: modification may be made in the above-mentioned embodiments, or equivalent replacement may be made to a portion or all of the technical features of the embodiments; the features in the embodiments of the present disclosure may be freely combined with each other without conflicting in configuration or principle; and such modifications or replacements may not depart from the scope of the embodiments of the present disclosure.

What is claimed is:

1. A sponge-based variable-stiffness support structure for natural orifice surgical instrument, configured to support the natural orifice surgical instrument comprising:
    a variable-stiffness sponge pipeline connected with the natural orifice surgical instrument and configured to support the natural orifice surgical instrument in a natural orifice;
    a first hydrophobic breathable film attached to an outer wall of the variable-stiffness sponge pipeline, and configured to isolate the variable-stiffness sponge pipeline from body fluid in the natural orifice; and
    a gas delivery assembly connected with the variable-stiffness sponge pipeline and configured to inject high-pressure air or water vapor into a variable-stiffness sponge pipe of the variable-stiffness sponge pipeline;
    wherein the variable-stiffness sponge pipeline has a stiffness inversely proportional to content of the water vapor.

2. The sponge-based variable-stiffness support structure for natural orifice surgical instrument according to claim 1, wherein a spring skeleton is provided in the variable-stiffness sponge pipeline and configured to support the variable-stiffness sponge pipeline.

3. The sponge-based variable-stiffness support structure for natural orifice surgical instrument according to claim 2, wherein the spring skeleton is made of stainless steel, and a surface of the spring skeleton is coated with an insulating coating.

4. The sponge-based variable-stiffness support structure for natural orifice surgical instrument according to claim 1, wherein an inner wall of the variable-stiffness sponge pipeline is provided with a second hydrophobic breathable film.

5. The sponge-based variable-stiffness support structure for natural orifice surgical instrument according to claim 4, wherein the gas delivery assembly comprises a gas delivery device and a gas delivery line, the gas delivery device being connected with the variable-stiffness sponge pipeline through the gas delivery line, and the gas delivery line being located in the variable-stiffness sponge pipe of the variable-stiffness sponge pipeline.

6. The sponge-based variable-stiffness support structure for natural orifice surgical instrument according to claim 5, wherein the gas delivery device comprises a water vapor generator configured to generate the water vapor therein and a gas pump configured to generate the high-pressure air.

7. The sponge-based variable-stiffness support structure for natural orifice surgical instrument according to claim 1, wherein a non-breathable film is attached locally to an inner wall of the variable-stiffness sponge pipeline and configured to isolate the water vapor from variable-stiffness sponge of the variable-stiffness sponge pipeline.

8. The sponge-based variable-stiffness support structure for natural orifice surgical instrument according to claim 1, wherein the variable-stiffness sponge pipeline has a cross-section of a circular ring, or an elliptical ring.

9. The sponge-based variable-stiffness support structure for natural orifice surgical instrument according to claim 1, wherein variable-stiffness sponge of the variable-stiffness sponge pipeline comprises polyvinyl formal.

10. A surgical instrument assembly, comprising: a natural orifice surgical instrument and the sponge-based variable-stiffness support structure for natural orifice surgical instrument according to claim 1, the sponge-based variable-stiffness support structure for natural orifice surgical instrument being connected with the natural orifice surgical instrument to support the natural orifice surgical instrument.

11. A method for using a sponge-based variable-stiffness support structure for natural orifice surgical instrument, comprising:
    assembling the sponge-based variable-stiffness support structure for natural orifice surgical instrument according to claim 1 with the natural orifice surgical instrument;
    injecting water vapor into the variable-stiffness sponge pipeline through a gas delivery line to make the variable-stiffness sponge pipeline flexible, and inserting the natural orifice surgical instrument into the natural orifice;
    adjusting a posture of the natural orifice surgical instrument, and injecting high-pressure air into the variable-stiffness sponge pipeline through the gas delivery line to make the variable-stiffness sponge pipeline stiff to perform operation;
    after completing the operation, injecting water vapor into the variable-stiffness sponge pipeline through the gas delivery line to make the variable-stiffness sponge pipeline return to being flexible, and retracting the surgical instrument from human body through the natural orifice.

12. The method for using a sponge-based variable-stiffness support structure for natural orifice surgical instrument according to claim 11, comprising:
attaching a non-breathable film to a portion of the variable-stiffness sponge pipeline that needs to be continuously maintained in a stiff state.

13. The method for using a sponge-based variable-stiffness support structure for natural orifice surgical instrument according to claim 11, wherein:
when the variable-stiffness sponge pipeline has an axial tensile elastic modulus between 0.09 and 10 MPa, the variable-stiffness sponge pipeline is in a flexible state; and,
when the variable-stiffness sponge pipeline has an axial tensile elastic modulus between 10 and 31 MPa, the variable-stiffness sponge pipeline is in a stiff state.

* * * * *